United States Patent
Kim et al.

(10) Patent No.: US 12,000,832 B2
(45) Date of Patent: Jun. 4, 2024

(54) MARKER COMPOSITION FOR DIAGNOSING OR PREDICTING PROGNOSIS OF LUNG CANCER BASED ON EXOSOME OVEREXPRESSING GCC2 GENE OR PROTEIN

(71) Applicants: KOREA UNIVERSITY RESEARCH AND BUSINESS FOUNDATION, Seoul (KR); KOREA ADVANCED INSTITUTE OF SCIENCE AND TECHNOLOGY, Daejeon (KR)

(72) Inventors: Hyun Koo Kim, Seoul (KR); Sung Hoi Hong, Seoul (KR); Yong Park, Seoul (KR); Yeon Ho Choi, Seoul (KR); Ji Ho Park, Daejeon (KR); Byeong Hyeon Choi, Seoul (KR); Hye Sun Jeong, Seoul (KR)

(73) Assignees: Korea University Research And Business Foundation, Seoul (KR); Korea Advanced Institute Of Science And Technology, Daejeon (KR)

( * ) Notice: Subject to any disclaimer, the term of this patent is extended or adjusted under 35 U.S.C. 154(b) by 134 days.

(21) Appl. No.: 17/539,030

(22) Filed: Nov. 30, 2021

(65) Prior Publication Data
US 2022/0196664 A1 Jun. 23, 2022

Related U.S. Application Data

(62) Division of application No. 16/762,140, filed as application No. PCT/KR2018/013220 on Nov. 2, 2018, now abandoned.

(30) Foreign Application Priority Data

Nov. 7, 2017 (KR) .......................... 10-2017-0147510

(51) Int. Cl.
C12Q 1/6886 (2018.01)
C07K 16/30 (2006.01)
G01N 33/574 (2006.01)

(52) U.S. Cl.
CPC ..... *G01N 33/57423* (2013.01); *C07K 16/3023* (2013.01); *C12Q 1/6886* (2013.01); *C12Q 2600/106* (2013.01); *C12Q 2600/118* (2013.01); *C12Q 2600/156* (2013.01)

(58) Field of Classification Search
CPC ................................................ G01N 33/57423
USPC .......................................................... 435/5
See application file for complete search history.

(56) References Cited

U.S. PATENT DOCUMENTS

| 7,897,356 | B2* | 3/2011 | Klass ................... C12Q 1/6811 435/7.1 |
| 2010/0047771 | A1 | 2/2010 | Yoon et al. |
| 2011/0038801 | A1 | 2/2011 | Jooss et al. |
| 2012/0058492 | A1* | 3/2012 | Lozupone ............ G01N 33/567 435/7.92 |
| 2012/0065100 | A1* | 3/2012 | Hoffmann .......... C12N 15/1137 530/389.7 |
| 2012/0065148 | A1* | 3/2012 | Hoffmann ........ G01N 33/57434 514/19.5 |
| 2014/0038901 | A1* | 2/2014 | Lyden .................. C12Q 1/6886 435/7.1 |

FOREIGN PATENT DOCUMENTS

| EP | 2728017 B1 | 8/2016 |
| KR | 100690250 B1 | 8/2006 |
| KR | 101371127 B1 | 3/2014 |
| KR | 101680360 B1 | 11/2016 |
| KR | 1020160133740 A | 11/2016 |
| WO | 2007026896 A1 | 3/2007 |
| WO | 2017181183 A1 | 10/2017 |

OTHER PUBLICATIONS

Jiang, Junhong et al., 'GCC2-ALK as a Targetable Fusion in Lung Adenocarcinoma and Its Enduring Clinical Responses to ALK Inhibitors', Lung Cancer, 2018 (online publication date: Oct. 27, 2017), vol. 115, pp. 5-11.
Vendrell, Julie A. et al, "Detection of Known and Novel ALK Fusion Transcripts in Lung Cancer Patients Using Next-generation Sequencing Approaches", Scientific Reports, 2017 (online publication date: Oct. 2, 2017), vol. 7, 12510, inner pp. 1-11.
Noh, Ka-Won et al., "Molecular breakdown: a comprehensive view of anaplastic lymphoma kinase (ALK)-rearranged non-small cell lung cancer", The Journal of Pathology, 2017 (online publication date: Sep. 28, 2017), vol. 243, pp. 307-319.
Reclusa et al. "Exosomes as diagnostic and predictive biomarkers in lung cancer", Journal of Thoracic Disease, 2017, vol. 9 (Suppl 13), S1373-S1382.
Taverna et al. "Exosomes isolation and characterization in serum is feasible in nonsmall cell lung cancer patients: critical analysis of evidence and potential role in clinical practice", Oncotarget, 2016, vol. 7, No. 19, p. 28748-28760.
Munagala et al. Tumor Biol, 2016, 37, p. 10703-10714.
English translation of International Search Report for International Patent Application No. PCT/KR2018/013220, dated Apr. 10, 2019, 2 pages.

* cited by examiner

*Primary Examiner* — Sean E Aeder
(74) *Attorney, Agent, or Firm* — Armstrong Teasdale LLP

(57) ABSTRACT

According to an embodiment of the present invention, a composition for diagnosing or predicting the prognosis of lung cancer is provided, the composition including a primer, probe, or antibody that specifically binds to a GRIP and coiled-coil domain-containing protein (GCC2) gene or protein in an exosome.

2 Claims, 4 Drawing Sheets

Specification includes a Sequence Listing.

MARKER COMPOSITION FOR DIAGNOSING OR PREDICTING PROGNOSIS OF LUNG CANCER BASED ON EXOSOME OVEREXPRESSING GCC2 GENE OR PROTEIN

This application is a divisional application of U.S. patent application Ser. No. 16/762,140, filed Aug. 14, 2020, which is a National Phase Application of PCT International Application No. PCT/KR2018/013220, having an International Filing Date of Nov. 2, 2018, which claims priority to Korean Patent Application No. 1020170147510, filed Nov. 7, 2017, each of which is hereby incorporated by reference in its entirety.

SEQUENCE LISTING

This application contains a sequence listing in computer readable format, the teachings and content of which are hereby incorporated by reference.

TECHNICAL FIELD

The following description relates to a marker composition for diagnosing or to prognosing lung cancer based on exosomes overexpressing a GCC2 gene or protein.

BACKGROUND ART

A tumor is a product of uncontrolled and disordered cell proliferation resulting from abnormal cell excess. When the tumor has disruptive proliferative, invasive and metastatic properties, the tumor is classified as a malignant tumor, that is, a cancer.

Currently, examination means for diagnosing cancer includes methods using X-ray imaging, endoscopy, biopsy, and the like. However, although these methods are relatively simple, the diagnosis success thereof is not high or the hygiene problem occurs. Further, a patient undergoes a pain in a process of the examination. Thus, a diagnosis method of cancer to replace the above methods is required.

In order to treat cancer, the diagnosis of cancer with high sensitivity and specificity is important in a pre-treatment stage. Only when the cancer is detected in an early stage thereof via the diagnosis, a cure success of the cancer is high.

Therefore, development of an early diagnosis method of cancer in a non-invasive manner, at a high sensitivity and at a high specificity is required. To date, there is no molecular diagnostic technique for early detection of lesion in a specific manner to determine whether the cancer occurs. Further, there is no method applicable to specific cancer in a specific manner.

DISCLOSURE OF INVENTION

Technical Goals

The present disclosure is to solve the above-mentioned problems of the prior art. A purpose of the present disclosure is to provide a marker composition that may be used in a non-invasive way while improving accuracy of lung cancer diagnosis.

However, a purpose of the present disclosure is not limited to the purpose as mentioned above. Other purposes as not mentioned will be clearly understood to those skilled in the art from the following descriptions.

Technical Solutions

According to an embodiment of the present disclosure, a marker composition is provided for diagnosing or prognosing lung cancer, the composition containing exosome overexpressing a GCC2 (GRIP and coiled-coil domain-containing protein) gene or protein.

According to an embodiment of the present disclosure, there is provided a composition for diagnosing or prognosing lung cancer, the composition containing a primer or a probe that specifically binds to a GCC2 (GRIP and coiled-coil domain-containing protein) gene in exosome.

According to an embodiment of the present disclosure, there is provided a composition for diagnosing or prognosing lung cancer, the composition containing an antibody that specifically binds to a GCC2 (GRIP and coiled-coil domain-containing protein) protein in exosome.

According to an embodiment of the present disclosure, a kit is provided for diagnosing or prognosing lung cancer, the kit containing the composition.

According to one embodiment of the present disclosure, the kit may be one or more selected from a group consisting of an RT-PCR kit, a microarray chip kit, a DNA kit and a protein chip kit.

According to an embodiment of the present disclosure, there is provided a method for providing information needed to diagnose or prognose lung cancer, the method including (a) separating an exosome from a biological sample; and (b) measuring an expression level of GCC2 (GRIP and coiled-coil domain-containing protein) gene or protein in the exosome.

According to an embodiment of the present disclosure, the biological sample may be one or more selected from a group consisting of whole blood, serum, plasma, saliva, urine, sputum, lymph and cell.

According to an embodiment of the present disclosure, a method for screening a lung cancer therapeutic agent is provided, the method including (a) treating a biological sample collected from a lung cancer patient with a candidate substance for a lung cancer therapeutic agent; (b) separating exosome from the biological sample; and (c) measuring an expression level of GCC2 (GRIP and coiled-coil domain-containing protein) gene or protein in the exosome.

Effects

The marker composition in accordance with the present disclosure contains gene or protein that is overexpressed in exosome of a lung cancer patient. Measuring the expression level thereof may allow diagnosing or prognosing the lung cancer in a non-invasive manner and at a high accuracy.

The effect of the present disclosure is not limited to the above effect and should be understood to include all of inferred effects from features of the present disclosure as set forth in the description or claims of the present disclosure.

BEST MODE FOR CARRYING OUT THE INVENTION

Figure 1:
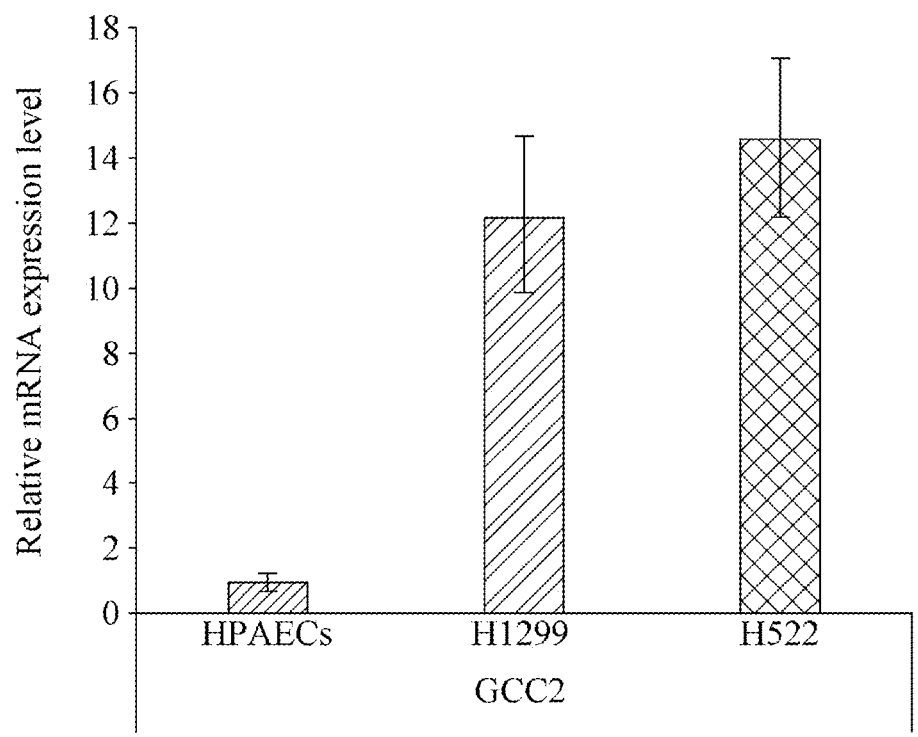
FIG. 1 shows the results of measuring the GCC2 gene expression level in the exosome according to an embodiment of the present disclosure.

Hereinafter, embodiments will be described in detail with reference to the accompanying drawings. Like reference numerals in the drawings denote like elements.

Various changes may be made to the embodiments described below. The embodiments as described below are not intended to limit the present disclosure. The present disclosure should be understood to include all modifications, equivalents, or substitutes of the embodiments.

The terminology used herein is for the purpose of describing particular embodiments only and is not intended to be limiting of the present disclosure. As used herein, an expression of the singular number is intended to include an expression of the plural number as well, unless the context clearly indicates otherwise. It will be further understood that the terms "including", "having", etc., when used in this specification, specify the presence of the stated features, numbers, steps, operations, constituent elements, parts, or combinations thereof disclosed in the specification, but do not preclude the presence or addition of one or more other features, numbers, steps, operations, constituent elements, parts, or combinations thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Further, in the description with reference to the accompanying drawings, the same components will have the same reference numerals and duplicate description thereof will be omitted. In the following description of the embodiment, when it is determined that the detailed descriptions of related known components may unnecessarily obscure the gist of the embodiment, the detailed description thereof will be omitted.

According to an embodiment of the present disclosure, a marker composition is provided for diagnosing or prognosing lung cancer, the composition containing exosome overexpressing a GCC2 (GRIP and coiled-coil domain-containing protein) gene or protein.

As used herein, the term "exosome overexpressing a GCC2 gene or protein" refers to exosome that expresses a higher level of the GCC2 gene or protein than exosome present in normal cells expresses.

An exosome refers to a nano-sized small endoplasmic reticulum (30 to 150 nm) secreted from most of cells. The exosomes and phospholipid bilayer are known to contain various kinds of proteins, genetic materials (DNA, mRNA, miRNA), lipids, etc. derived from cells. Further, it has been reported that exosomes derived from tissues may be used to diagnose diseases because the exosomes derived from the tissues reflect the state of the tissues secreting the exosomes.

The present inventors confirmed that using the GCC2 gene or protein specifically expressed from lung cancer-derived exosomes may allow accurately and quickly diagnosing or prognosing the lung cancer. In this way, the present disclosure has been completed.

As used herein, the term "diagnosis" refers to identifying the presence or characteristic of a pathological condition, that is, whether the lung cancer occurs. Further, "prognosis" refers to determining the recurrence, metastasis, drug responsiveness, and resistance of the subject after treatment of lung cancer. The "prognosis" may include measuring the expression level of GCC2 in the exosomes isolated from the subject's sample, thereby to not only predict whether the subject has lung cancer, but also predict whether the subject is likely to have a good survival prognosis in the future.

Since the lung cancer may be diagnosed or prognosed based on the measuring result of the expression level of the GCC2 gene or protein, primers or probes that specifically bind to the gene, or antibodies that specifically bind to the protein may be used as the composition for diagnosing or prognosing the lung cancer.

In addition, a kit for diagnosing or prognosing lung cancer may be provided by applying a primer or a probe specifically binding to the GCC2 gene, or an antibody specifically binding to the GCC2 protein to a kit.

The kit may include, but is not limited to, an RT-PCR kit, a microarray chip kit, a DNA kit, a protein chip kit, and the like. The kit may check and detect the expression level in the exosome of the GCC2 gene or protein corresponding to the marker to diagnose or prognose lung cancer based on the expression level.

The kit may include primers, probes or antibodies that selectively recognize markers for the diagnosis or prognosis of lung cancer, as well as one or more other component compositions, solutions, or devices suitable for analytical methods.

Further, the kit may include a substrate, a suitable buffer solution, a secondary antibody labeled with a chromogenic enzyme or a fluorescent substance, and a chromogenic substrate for immunological detection of the antibody. The substrate may include a nitrocellulose membrane, a 96 well plate synthesized with a polyvinyl resin, a 96 well plate synthesized with a polystyrene resin, a slide glass made of glass, and the like. The chromogenic enzyme may include peroxidase, alkaline phosphatase, etc. The fluorescent substance may include FITC, RITC, etc., and the chromogenic substrate may include ABTS (2,2'-azino-bis-(3-ethylbenzothiazoline-6-sulfonic acid)) or OPD (O-phenylenediamine), TMB (tetramethyl benzidine).

According to an embodiment of the present disclosure, a method of providing information necessary for diagnosing or prognosing lung cancer is provided. The method includes (a) separating an exosome from a biological sample; and (b) measuring an expression level of a GCC2 (GRIP and coiled-coil domain-containing protein) gene or protein in the exosome.

The biological sample may be one or more selected from a group consisting of whole blood, serum, plasma, saliva, urine, sputum, lymph, and cells, preferably, whole blood or cells. However, the present disclosure is not limited thereto.

The gene expression level measurement includes a process of identifying the presence and the expression level of mRNA of the GCC2 gene in a biological sample for diagnosing or prognosing the lung cancer, and may mean measuring mRNA expression level.

Analytical methods for the gene expression level measurement may include reverse transcriptase PCR (RT-PCR), competitive reverse transcriptase PCR (Competitive RT-PCR), real-time reverse transcriptase (Real-time RT-PCR), RNase protection assay (RPA), northern blotting, DNA chips and the like, but is not limited thereto.

Further, the protein expression level measurement refers to a process of identifying the presence and the expression level of the GCC2 protein in a biological sample for diagnosing or prognosing the lung cancer.

The expression level measurement or comparative analysis method of the protein may include protein chip analysis, immunoassay, ligand binding assay, Matrix Assisted Laser Desorption/Ionization Time of Flight Mass Spectrometry (MALDI-TOF), and Surface Enhanced Laser Desorption/Ionization Time of Flight Mass Spectrometry (SELDI-TOF), radioimmunoassay, radial immunodiffusion, Ouchterlony immunodiffusion, rocket immunoelectrophoresis, tissue immunostaining, complement fixation analysis, two-dimensional electrophoresis, liquid chromatography-mass spectrometry (LC-MS), liquid chromatography-mass spectrometry/mass spectrometry (LC-MS/MS), western blotting, and enzyme-linked immunosorbentassay (ELISA), and the like, but is not limited thereto.

After the gene or protein expression level of the GCC2 is measured and then when the expression level is higher than that of a normal control group, it may be determined that the lung cancer has occurred or is more likely to occur.

Further, according to an embodiment of the present disclosure, a method for screening a lung cancer therapeutic agent is provided, the method including (a) treating a biological sample collected from a lung cancer patient with a candidate substance for a lung cancer therapeutic agent; (b) separating exosome from the biological sample; and (c) measuring an expression level of a GCC2 (GRIP and coiled-coil domain-containing protein 2) gene or protein in the exosome.

In an extension of the method of providing the information necessary for diagnosing or prognosing lung cancer, the process of screening the candidate substance for the lung cancer therapeutic agent may be applied. That is, after treating the biological sample isolated from a lung cancer patient with the candidate substance for the lung cancer therapeutic agent, and then when the expression level of the GCC2 gene or protein in the exosome present in the biological sample decreases, it may be identified that the candidate substance effectively functions as the lung cancer therapeutic agent.

Hereinafter, the present disclosure will be described in more detail with reference to Examples. The following examples are described for the purpose of illustrating the present disclosure, but the scope of the present disclosure is not limited thereto.

Example 1: Exosome Isolation and Protein Analysis Preparation

Each of five lung cancer cell lines (H522, A549, H1650, PC9, H1299) was cultured in a dish of 150 mm in diameter. At this time, the supernatant of FBS (Fetal Bovine Serum) from which exosomes were removed via centrifugation at 120,000 g for 4 hours using an ultrafast centrifuging device was used as a culture solution. The culture solution was used to continuously culture the cell lines for 2 to 3 days so that the cells were brought into a 70 to 80% confluency state.

The obtained culture solution was centrifuged at 10,000 g for 30 minutes to remove cell debris, and sequentially passed through 0.45 μm and 0.22 μm filters to remove relatively bulky materials. The filtered cell culture solution was then concentrated using Amicon tube 100K (Millipore, USA) while leaving only particles of the desired size.

Next, only particles of exosome size (50 nm to 100 nm) were separated from the concentrated cell culture solution using column liquid chromatography, and then the cell culture solution was concentrated again using Amicon tube 100K.

RIPA lysis buffer (Thermo Fisher Scientific, USA) was applied to the concentrated exosome to obtain protein, which was commissioned to the Korea Basic Science Institute (KBSI) to obtain protein analysis results.

Based on these results, a GCC2 (GRIP and coiled-coil domain-containing protein) possibly related to a process of generation of exosome was finally selected among the five proteins expressed only in the lung cancer cell lines.

Next, in order to identify the characteristics of exosomes isolated from the plasma of lung cancer patients, blood was collected from 20 patients with lung cancer in the 1st to 3rd stages, and then exosome was isolated from the plasma using Exoquick (Systembio, USA).

Example 2: Intracellular GCC2 Gene Expression Level Measurement

In order to identify the intracellular expression level of the GCC2 gene selected according to Example 1, quantitative reverse transcriptase PCR (qRT-PCR) was performed.

Specifically, RNA was isolated using Trizol (Thermo Fisher Scientific, USA) according to the manufacturer's instructions, and then, 50 ng/100 μl of cDNA was obtained using reverse transcription polymerase chain reaction (RT-PCR).

qRT-PCR was performed three times using a KAPA SYBR FAST qPCR Master Mix (2×) kit on a StepOne Plus Real-Time PCR System (Applied Biosystems, CA) according to the manufacturer's instructions. The base sequences of the primer pairs used in the reaction are shown in Table 1 below, and the results of qRT-PCR are shown in FIG. 1.

TABLE 1

| Primer | Base sequence |
| --- | --- |
| GCC2-Forward | 5'-CGAGCTGTAGCTATGGAGACG-3' (SEQ ID NO. 1) |
| GCC2-Reverse | 5'-CGTAGGCTCTACTGCAGGTC-3' (SEQ ID NO. 2) |

Referring to FIG. 1, it may be seen that expression of GCC2 in the lung cancer cell line is higher than that in normal cell lines (HPAECs). These results suggest that the GCC2 gene expression level may provide information necessary for the diagnosis or prognosis of lung cancer.

Example 3: Exosome Secretion Measurement

Since GCC2 is a protein that is estimated to be related to exosome production, exosome secretion was measured in normal cell lines (HPAECs) and lung cancer cell lines (H1299, H522). Exosome secretion was measured indirectly using DLS (Dynamic Light Scattering).

Specifically, after seeding the same amounts of normal cell lines and lung cancer cell lines, the cell lines were exposed to the culture solution of 1.5 ml for 24 hours. Then, only the exosome was separated from 1 ml of the culture solution without concentration, and then a count rate was measured using DLS. The presence of a large number of particles in the solution increases the count rate. This allows indirect comparison between the amounts of exosomes in the cell lines. Further, the particle amount was calculated based on an average obtained by dividing the count rate based on the number of cells at the time when the culture solution was collected. The results are shown in Table 2 and FIG. 2 below.

TABLE 2

| Cell | HPAECs | H1299 | H522 |
|---|---|---|---|
| Seeding | 100,000 | 100,000 | 100,000 |
| Count rate | 545,000 | 1,080,000 | 650,000 |
| Average | 3.05 | 8.05 | 16.8 |
| CR/# | 0.559633 | 0.74537 | 2.584615 |

Figure 2:
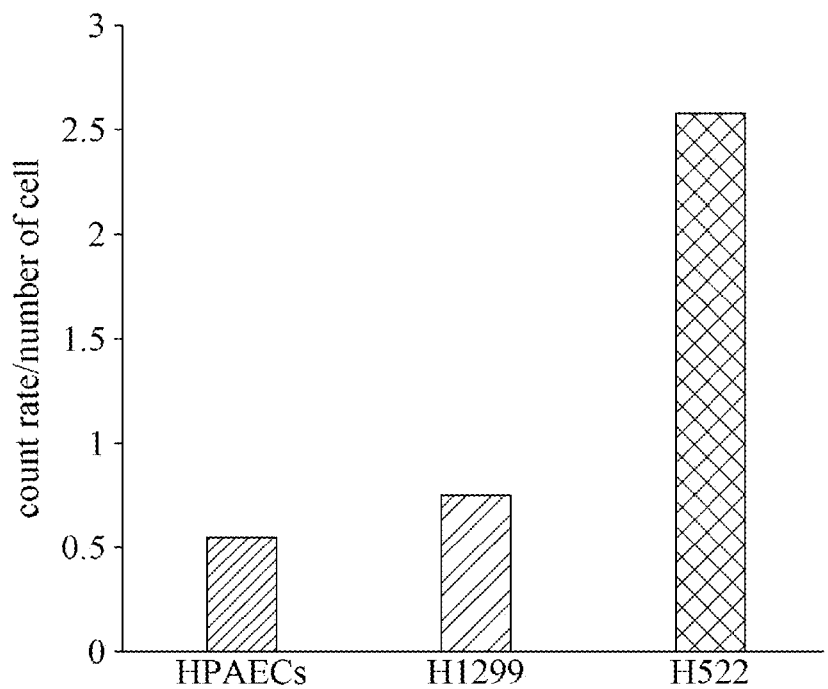
FIG. 2 shows the results of measuring the exosome secretion according to an embodiment of the present disclosure.

Referring to Table 2 and FIG. 2, it may be identified that the lung cancer cell line has a larger amount of particles than that of the normal cell line. This means that the lung cancer cell line has more active exosome secretion than the normal cell line has. Based on these results, it may be expected that the GCC2 expressed only in exosome of the lung cancer cell line affects exosome secretion.

Example 4: Measurement of GCC2 Protein Expression Level in Exosome

Western blotting was performed to identify the expression level of the GCC2 protein in the exosome obtained according to Example 1.

Specifically, exosomes were extracted from the lung cancer cell lines and normal cell lines using RIPA lysis buffer containing a proteinase inhibitor cocktail, and each of the exosomes was lysed to obtain protein.

Figure 3:
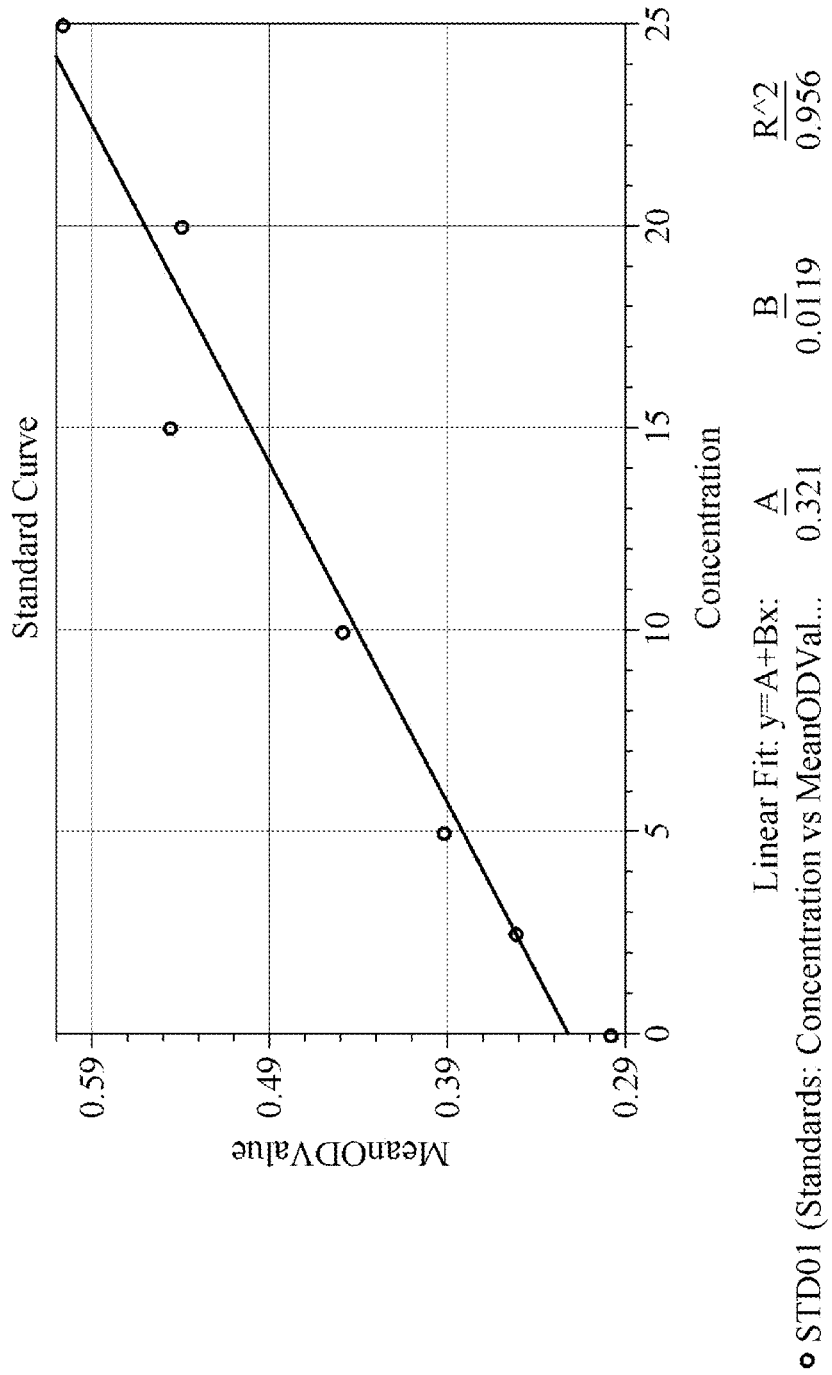
FIG. 3 is a standard curve calculated for quantification of GCC2 protein in the exosome according to an embodiment of the present disclosure.

The obtained protein was quantified using the Bradford assay method. The standard curve is obtained as shown in FIG. 3, where y=0.321+0.0119x and an R-square value is 0.956.

The proteins obtained from the exosomes were diluted at a 1:100 ratio and were quantified. OD values as shown in Table 3 below were obtained. The concentrations of HPAECs, H1299, and H522 were calculated to be 1013.574 µg/ml 2318.93 µg/ml and 2137.177 µg/ml, respectively. Based on this result, a sample was prepared by inactivating each of 20 µg of protein obtained from cells and 15 µg of protein obtained from exosomes with heat.

TABLE 3

| Cells | HPAECs | H1299 | H522 |
|---|---|---|---|
| OD value | 0.4415 | 0.5975 | 0.576 |

Total protein lysates were loaded on 10% SDS-PAGE gel on a lane basis and fractionated based on a size. The separated protein was attached to a PVDF membrane and blocked with tris-buffered saline-Tween 20 containing 5% skim milk. The PVDF membrane was treated overnight at 4 with GCC2 (1:500, Santa Cruz), CD63 (1:500, Santa Cruz), α-tubulin (1:500, Santa Cruz) primary antibodies. Then, the PVDF membrane was treated with anti-rabbit IgG-HRP binding secondary antibody, and then was washed and reacted with ECL buffer (Bio-rad, USA). Images obtained using FluorChem E system (proteinsimple, USA) are shown in FIG. 4.

Figure 4:
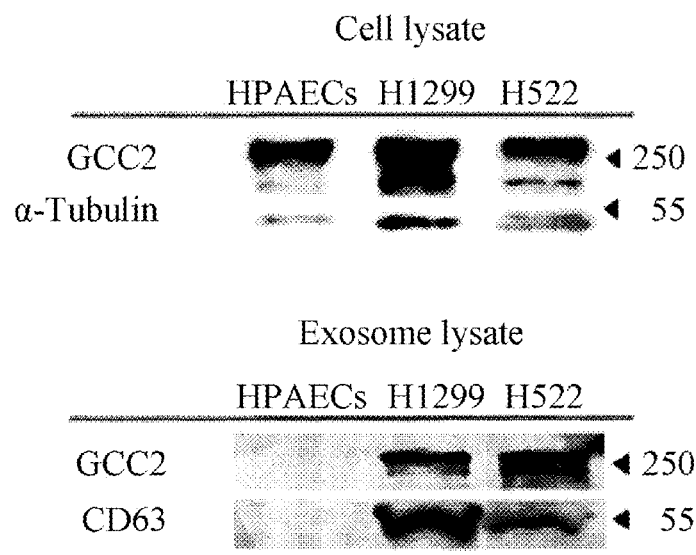
FIG. 4 shows the results of measuring the GCC2 protein expression level in the exosome according to an embodiment of the present disclosure.

Referring to FIG. 4, the cell lysate showed no difference between GCC2 protein expression levels in the normal cell line and lung cancer cell line, but the exosome lysate showed a similar pattern to that of CD63 as an exosome marker.

Based on this result, it may be seen that the protein percentages in the normal cells and lung cancer cells in the same amount of the protein are not equal to each other, and the GCC2 protein shows a similar tendency to that of the exosome marker CD63. That is, it was identified that the cancer cells have a protein percentage different from that in the normal cells, and in particular, the GCC2 is strongly expressed in the cancer cells.

Example 5: Measurement of GCC2 Protein Expression Level in Blood-Derived Exosomes In order to identify whether exosomes containing the GCC2 protein could be used as a marker for diagnosing or prognosing the lung cancer, the following experiments were performed.

GCC2 poly clonal antibody was applied to a 96 well plate at 0/N such that the plate was coated with the GCC2 poly clonal antibody. Then, wells were blocked from each other using a blocking solution. After extracting exosomes from the bloods of the lung cancer stage 1 to 3 patients and post-operative patients and the normal people, 50 µl of the exosome was added to each well and reacted for 2 hours and washed thoroughly. Afterwards, a monoclonal GCC2 antibody was used as a detection antibody to identify the GCC2 protein of exosomes. Standard GCC2 solution was used to draw a standard curve. Then, an expression level of the GCC2 protein in the in-blood exosome was calculated using a trend line (y=0.008x+0.1157, $R^2$=0.9937) of the standard curve.

Figure 5:
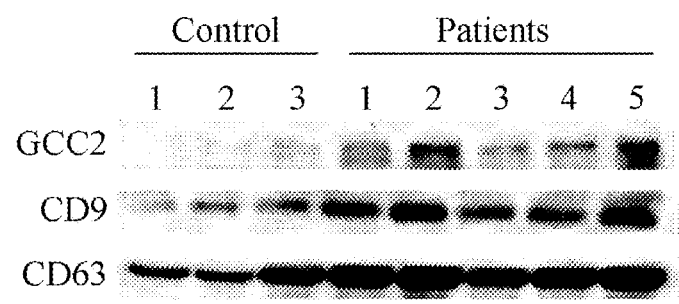
FIG. 5 shows the results of Western blot measurement of the GCC2 protein expression level in the exosome according to an embodiment of the present disclosure.

From a result of identifying protein expression levels in the exosomes extracted from the bloods of the normal group (n=4) and the lung cancer patient group (n=20), it was confirmed that the expression of GCC2 was increased in the lung cancer patient group (FIG. 5).

Figure 6:
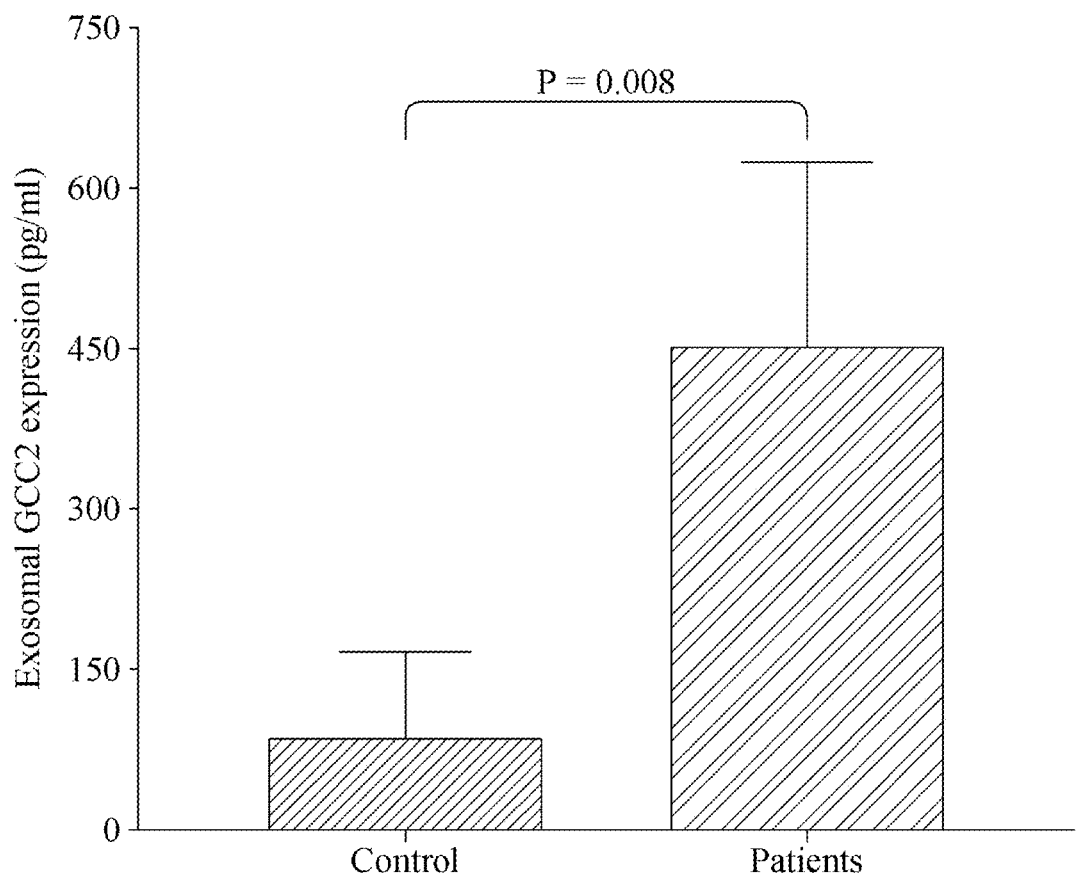
FIG. 6 shows the ELISA results of measuring the GCC2 protein expression level in the exosome according to an embodiment of the present disclosure.

Further, from the result of performing ELISA (Enzyme linked immunoassay) analysis on the same subject, it was identified that the expression of GCC2 was increased in the lung cancer patient group (FIG. 6).

Figure 7:
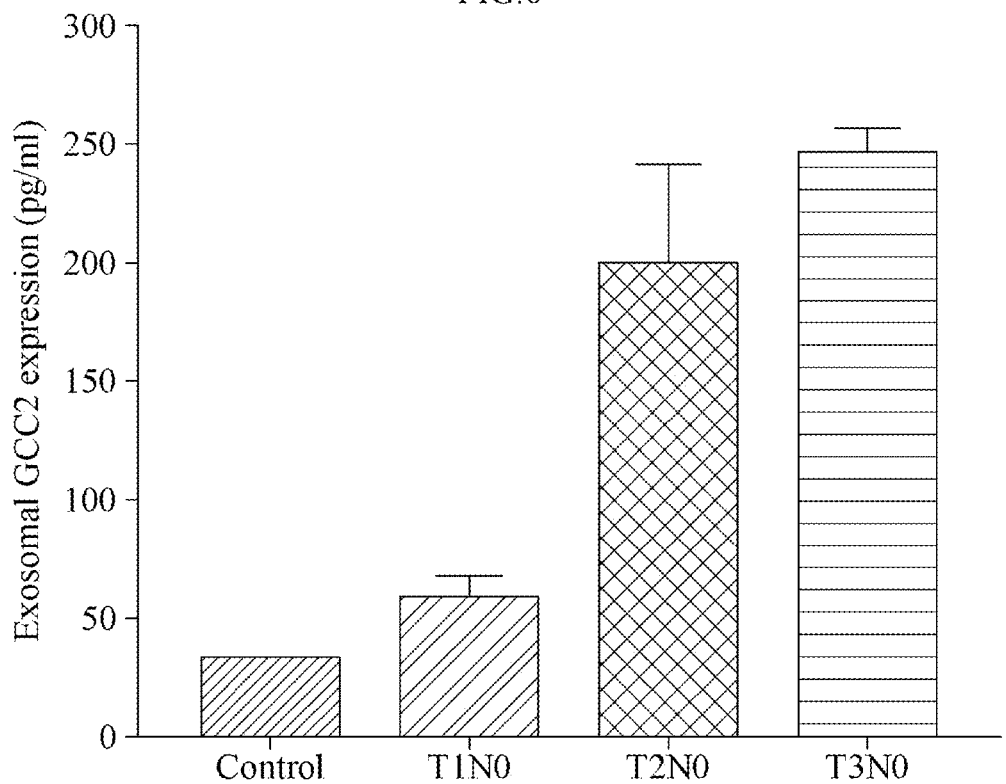
FIG. 7 shows the ELISA results of measuring the GCC2 protein expression level in the exosome based on the stages of cancer progression according to an embodiment of the present disclosure.

On the other hand, the GCC2 showed low sensitivity in early lung cancer (T1N0) and showed high sensitivity in the stage 3 cancer (T3N0). The sensitivity increased significantly in the metastatic cancer state compared to the normal state (FIG. 7).

Although the present disclosure has been described with reference to the limited Examples and drawings, various modifications and variations may be made by those skilled in the art from the above description. For example, although the embodiment may be performed in a different order than the described order, and/or the described components may be combined with each other in a different form than the described from, or may be replaced or substituted by other components or equivalents, appropriate results may be achieved.

Therefore, other implementations, other Examples, and equivalents to the claims are within the scope of the following claims.

The invention claimed is:

1. A method for identifying a level of GCC2 expression, the method comprising below steps:
(a) obtaining a blood sample from a suspected lung cancer subject;
(b) separating an exosome from the blood sample; and
(c) measuring an expression level of a GCC2 (GRIP and coiled-coil domain-containing protein) protein in the exosome.

2. The method of claim 1, wherein the (b) step is performed by using a composition containing an antibody that specifically binds to a GCC2 protein.

* * * * *

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: GCC2 Forward Primer

<400> SEQUENCE: 1
cgagctgtag ctatggagac g                                       21

<210> SEQ ID NO 2
<211> LENGTH: 20
<212> TYPE: DNA
<213> ORGANISM: Artificial Sequence
<220> FEATURE:
<223> OTHER INFORMATION: GCC2 Reverse Primer

<400> SEQUENCE: 2
cgtaggctct actgcaggtc                                         20
```